US00PP12295P2

(12) United States Plant Patent
Utecht

(10) Patent No.: US PP12,295 P2
(45) Date of Patent: Dec. 18, 2001

(54) GERANIUM PLANT NAMED 'FISCORAL'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/323,151

(22) Filed: Jun. 1, 1999

(51) Int. Cl.[7] ..... A01H 5/00
(52) U.S. Cl. ..... Plt./332
(58) Field of Search ..... Plt./332, 324

(56) References Cited

FOREIGN PATENT DOCUMENTS 98-1356 * 4/1998 (CA) .
98-26-1421 * 4/1998 (CH) .
PEL 1356 * 9/1996 (DE) .
97/0954 * 9/1997 (EP) .
465 * 12/1998 (PL) .

OTHER PUBLICATIONS

Pelargonium 1998, Pelfi Fischer, Hillscheid Germany, p. 17 (1998/1999).*
Licensing agreement, http://www.sicasov.com/baremes/fl9899.htm., 1998/1999.*
UPOV–ROM GTIM Computer Database 1999/02, GTI Jouve Retrieval Software, citation for 'Fiscoral', 1996–1998.*

* cited by examiner

*Primary Examiner*—Bruce R. Campell
*Assistant Examiner*—Anne Marie Grünberg
(74) *Attorney, Agent, or Firm*—Florfis AG

(57) ABSTRACT

A new and distinct cultivar of geranium plant named 'Fiscoral', as described and illustrated, and particularly characterized by the combined features of orange-red flower color, double flower form, compact, rounded inflorescence, intense green foliage with slight zonation, and moderately vigorous growth, in combination with a well-branched and uniformly developed plant habit.

2 Drawing Sheets

BACKGROUND OF THE INVENTION

The present invention comprises a new and distinct cultivar of geranium plant, botanically known as *Pelargonium peltatum*, and hereinafter referred to by the cultivar name 'Fiscoral'.

'Fiscoral' is a product of a planned breeding program which had the objective of creating a geranium variety with orange-red flower color and well-branched, moderately tall, bushy, moderately-compact growth habit.

'Fiscoral' was originated from a hybridization made by the inventor, Angelika Utecht, in a controlled breeding program in Galdar, Gran Canaria, Spain, in 1994. The female parent was the patented variety 'Fizzard' (U.S. patent application Ser. No. 08/968,044) which is characterized by having a single form, bright red flowers, intense green, slightly zoned foliage, vigorous growth, and very early flowering response. The male parent of 'Fiscoral' was the commercial variety 'Gauguin', the original name used in Europe and known commercially in the United States as 'Nanette' (U.S. Plant Pat No. 7,360) and designated as 'Guitari' for Plant Breeders' Rights application, which is characterized by orange-red semi-double flowers, medium green foliage with slight zonation and moderately vigorous growth.

'Fiscoral' was selected as one flowering plant within the progeny of the stated cross by the inventor, Angelika Utecht, in spring 1995 in a controlled environment in Galdar, Gran Canaria, Spain.

The first act of asexual reproduction of 'Fiscoral' was accomplished when vegetative cuttings were taken from the initial selection in May 1995 in a controlled environment in Galdar, Gran Canaria, Spain by Angelika Utecht. Horticultural examination of plants grown from cuttings of the clone initiated in May 1996 in Hillscheid, Federal Republic of Germany, and continuing thereafer, has demonstrated that the combination of characteristics as herein disclosed for 'Fiscoral' are firmly fixed and are retained through successive generations of asexual reproduction.

BRIEF DESCRIPTION OF THE INVENTION

The following traits have been repeatedly observed and are determined to be basic characteristics of 'Fiscoral', which in combination distinguish this geranium as a new and distinct cultivar:

1. orange-red flower color;
2. double, slightly zygomorphic flowers in compact semi-spherically shaped umbels (inflorescence);
3. intense medium-green colored foliage with narrow, ring-shaped zonation;
4. vigorous growth;
5. well-branced, dense and uniformly developed plant habit; and
6. early flowering response.

'Fiscoral' has not been observed under all possible environmental conditions. The phenotype of the new cultivar may vary significantly with variations in environment such as temperature, light intensity and daylength without any change in genotype of the plant. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fiscoral' is the paternal variety 'Gauguin' ('Nanette'/ 'Guitari'). In comparison to 'Gauguin', 'Fiscoral' has:

(a) A similar flower color, but somewhat differently shaped corolla, it is more zygomorph, in contrast to the nearly round floret of 'Gauguin', it has narrower but longer petals, and somewhat stronger markings on petals;
(b) Longer and thinner peduncles and slightly larger umbels;
(c) Darker-green pedicels with 'swellings/joints' and with a slight infusion of anthocyanin ('Gauguin' is without swellings and without anthocyanin);
(d) Smaller and more intensely green colored leaves; and
(e) 25–30% more branches resulting in an even bushier and more uniform plant habit.

BRIEF DESCRIPTION OF THE DRAWING

The accompanying color photographic drawings show typical flower and foliage characteristics of 'Fiscoral' with colors being as true as possible with illustrations of this type.

FIG. 1 is a side view of the plant in a hanging basket.

FIG. 2 is a close-up view of the inflorescence of 'Fiscoral'.

DETAILED BOTANICAL DESCRIPTION

The measurements were taken in Langley, British Columbia, Canada, on May 26, 1998, 10 weeks after planting of rooted cuttings into 15-cm pots. The plants had not been pinched. In the following description, color references are made to The Royal Horticutural Society Colour Chart (R.H.S.). The color values were determined indoors from flowers developed in a greenhouse in May 1998 in Hillscheid, Germany.

Classification:

*Botanical.*—A hybrid of the species *Pelargonium peltatum L'Hérit.*

*Commerical.*—Ivy geranium, cv. 'Fiscoral'.

Inflorescence:

*Umbel.*—Shape: Semi-spherical. Average diameter: 83 mm. Average depth: 45 mm. Peduncle length: 213 mm. Peduncle color: Light-green, RHS 143 B–C. Peduncle texture: Smooth, slightly glossy, with no or very weak pubescence. Pedicel length: 21 mm. Pedicel color: Light-green, RHS 143 B–C with the 'joint', may be reddish brown, about RHS 180B–180C when partly infused with anthocyanin. Number of flowers per umbel: Approximately 11–18. Lastingness of the individual umbel: 15 flowers or buds in various stages of development; the individual umbel lasts approximately 15 days in greenhouse conditions in spring at a temperature of 18° C.

*Corolla.*—Average diameter: 48 mm. Form: Double (due to the number of petals), though the appearance is that of a semi-double floret. Shape: Medium-sized, slightly zygomorphic floret, with an open center (middle of the flower) and often a gap between upper and lower petals; the petals are relatively narrow and may appear slightly serrated at the tip. Number of petals: 11–14. Number of petaloids: 1–3. Color (general tonality from a distance of three meters): Orange-red, RHS 43 A–43 B. Color of upper petals: RHS 43 A–B. Markings of upper petals: Relatively weak, two dark-red stripes (veins), RHS 46 A, with a lighter spot between, and with a small cherry red spot, RHS 46 B or slightly more bluish, in the middle of the petal. Color of lower petals: RHS 43 A–B, no markings. Color of lower surface of petals: RHS 43 B–C. Color of sepals: Light to medium green, RHS 143 A–B, the largest sepal is green to light-red, RHS 179 B, due to infusion of anthocyanin. Number of sepals: 5 (occasionally 6). Texture of sepals: Smooth surface with moderate pubescence.

*Bud (just before petals unfold).*—Shape: Narrow elliptical. Color (sepals): Green, RHS 143 A–B. Color (petals): Orange-red to red, RHS 43 A. Length: Approximately 20 mm. Width: Approximately 8–9 mm.

*Reproductive organs.*—Androecium: Approximately 5 fertile anthers, white to light-pink filaments, yellow-orange pollen. Gynoecium: 5–6-lobed stigma, red in color (RHS 43 A) and whitish style. Fertility/seed set: May occur in late summer and fall, but not to such a degree as to affect development of new flowers.

*Spring flowering response period.*—In Hillscheid, Germany, in 1998, plants had on average 1.0 flowers opened 15 weeks after planting of unrooted cuttings.

*Outdoor flower production.*—Rich.

*Blooming habit.*—Continuous flowering from about May to mid-September; after which flowering may be poor depending on general conditions and light intensity. There is no fragrance noticeable.

*Lastingness of the individual bloom.*—The flower is not completely resistant against shattering (floret easily dropping its petals), but it has relatively good rain resistance and it is not very susceptible to getting burned/scorched by the sun; the bloom lasts approximately 8 days in greenhouse conditions in spring at a temperature of 18° C.

*Durability.*—Average shatter resistance, rain resistance fair for a double-flowered cultivar.

Plant:

*Foliage.*—Form: Ivy-shaped, distinctly lobed, with closed to slightly overlapping base. Margin: Entire, except for single notches or slight serration near the tips of lobes. Size of leaf: 86 mm wide. Texture: Smooth surface, waxy, no pubescence. Color of upper surface: Intense medium-green, approximately RHS 137 B–C. Color of lower surface: RHS 137 C–D. Zonation: Narrow, ring-shaped, brown, approximately RHS 166 A, distinctness is weak to medium. Tolerance of botrytis: Good.

*General appearance and form.*—Habit: Moderately tall, fairly round, bushy, moderately compact and moderately trailing. Internode length: 40–60 mm. Branching pattern: 5.2 naturally-occurring branches. Length of branches: 65 cm (in late August, based on 32-week-old plants).

I claim:

1. A new and distinct cultivar of geranium plant named 'Fiscoral', as described and illustrated.

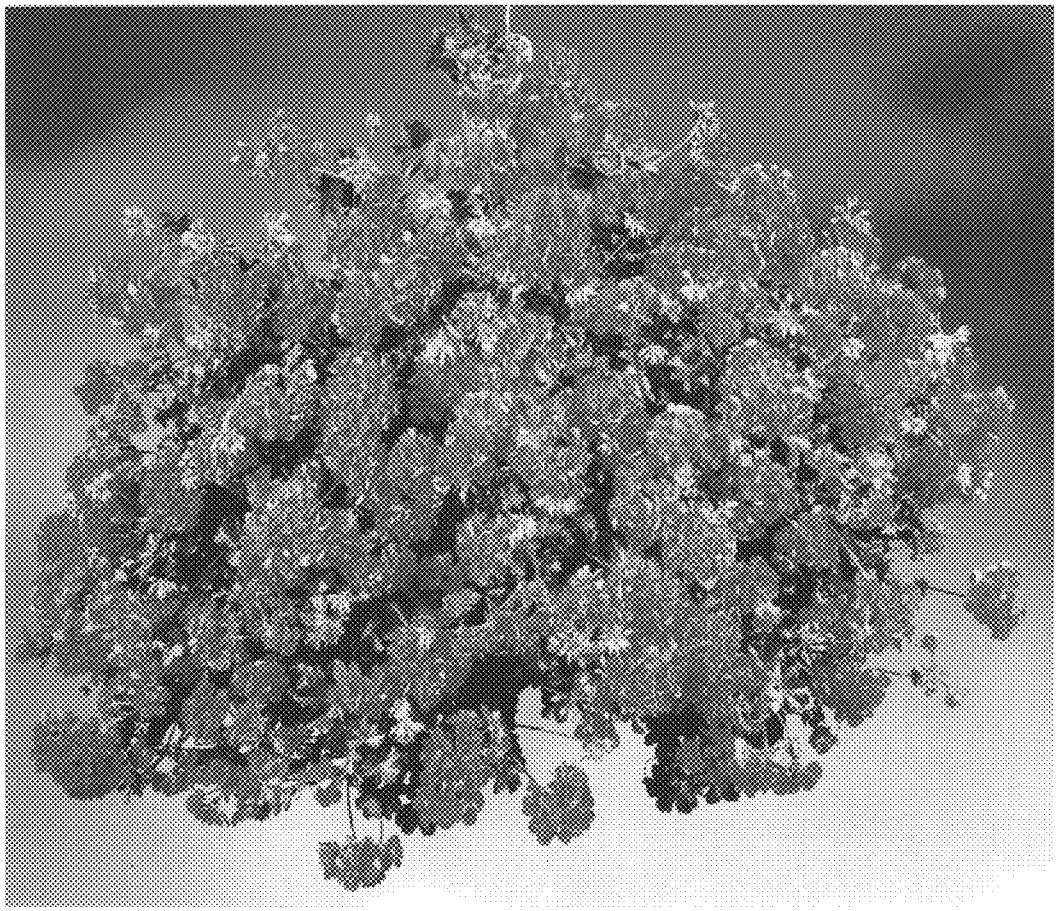

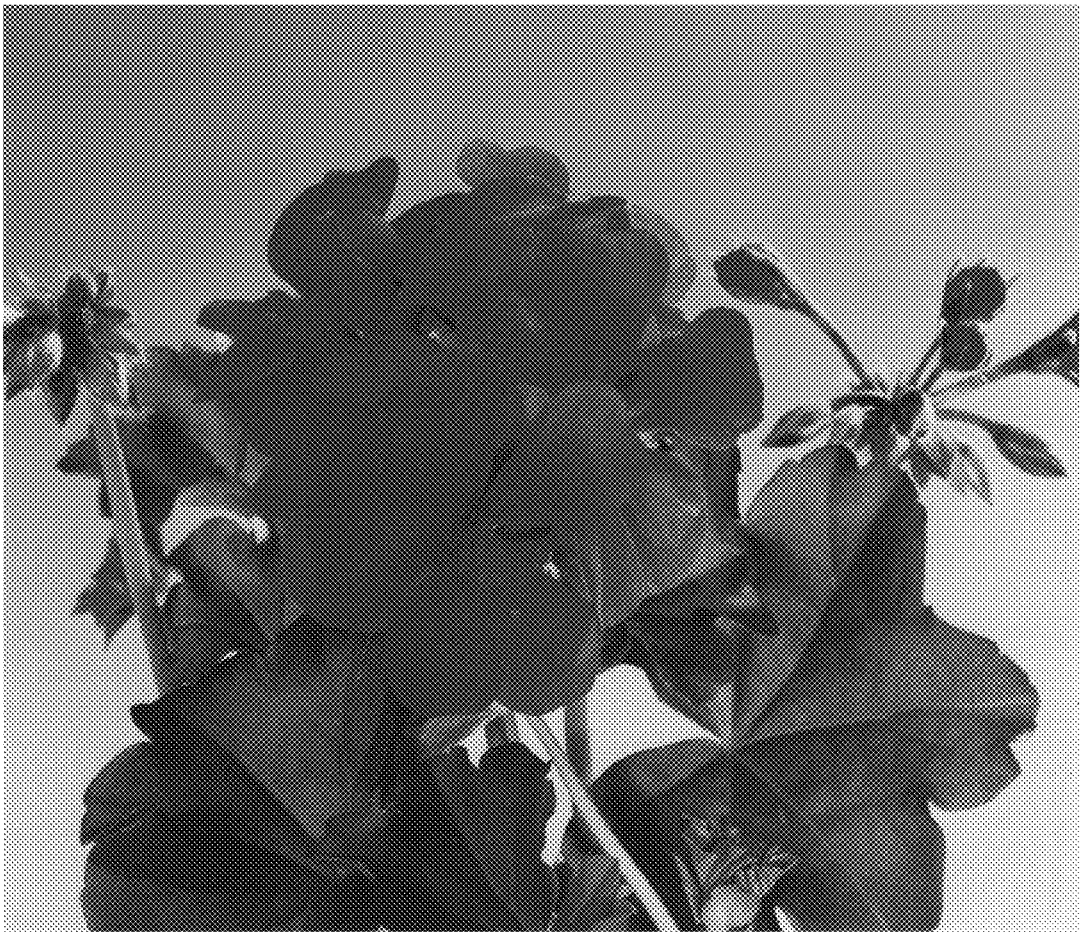

* * * * *